(12) United States Patent
Chen et al.

(10) Patent No.: US 7,665,844 B2
(45) Date of Patent: Feb. 23, 2010

(54) HIGH-RESOLUTION ADAPTIVE OPTICS SCANNING LASER OPHTHALMOSCOPE WITH MULTIPLE DEFORMABLE MIRRORS

(75) Inventors: Diana C. Chen, Fremont, CA (US); Scot S. Olivier, Livermore, CA (US); Steven M. Jones, Livermore, CA (US)

(73) Assignee: Lawrence Livermore National Security LLC, Livermore, CA (US)

( * ) Notice: Subject to any disclaimer, the term of this patent is extended or adjusted under 35 U.S.C. 154(b) by 0 days.

(21) Appl. No.: 11/874,832

(22) Filed: Oct. 18, 2007

(65) Prior Publication Data

US 2008/0218694 A1   Sep. 11, 2008

Related U.S. Application Data

(60) Provisional application No. 60/852,857, filed on Oct. 18, 2006.

(51) Int. Cl.
*A61B 3/14*   (2006.01)
*A61B 3/10*   (2006.01)
*A61B 3/00*   (2006.01)

(52) U.S. Cl. .................... 351/206; 351/221; 351/246
(58) Field of Classification Search .......... 351/205–246
See application file for complete search history.

(56) References Cited

U.S. PATENT DOCUMENTS

| 6,609,794 | B2 * | 8/2003 | Levine | 351/221 |
| 6,890,076 | B2 | 5/2005 | Roorda | |
| 7,118,216 | B2 * | 10/2006 | Roorda | 351/205 |
| 2004/0239876 | A1 | 12/2004 | Levine | |

\* cited by examiner

*Primary Examiner*—Mohammed Hasan
(74) *Attorney, Agent, or Firm*—John P. Wooldridge; John H. Lee

(57) ABSTRACT

An adaptive optics scanning laser ophthalmoscopes is introduced to produce non-invasive views of the human retina. The use of dual deformable mirrors improved the dynamic range for correction of the wavefront aberrations compared with the use of the MEMS mirror alone, and improved the quality of the wavefront correction compared with the use of the bimorph mirror alone. The large-stroke bimorph deformable mirror improved the capability for axial sectioning with the confocal imaging system by providing an easier way to move the focus axially through different layers of the retina.

25 Claims, 4 Drawing Sheets

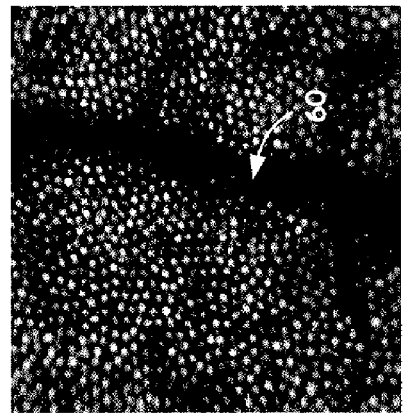
Fig. 2(c)
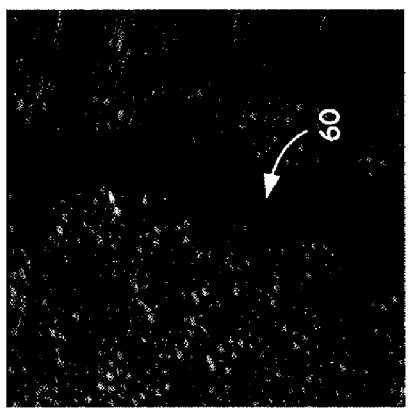
Fig. 2(b)
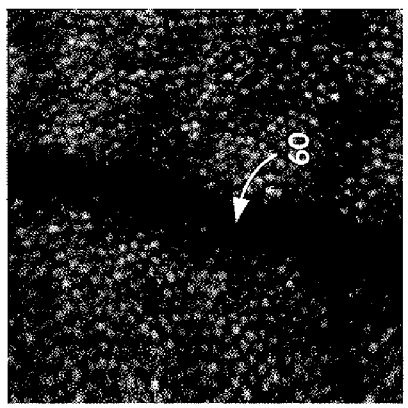
Fig. 2(a)
Fig. 2

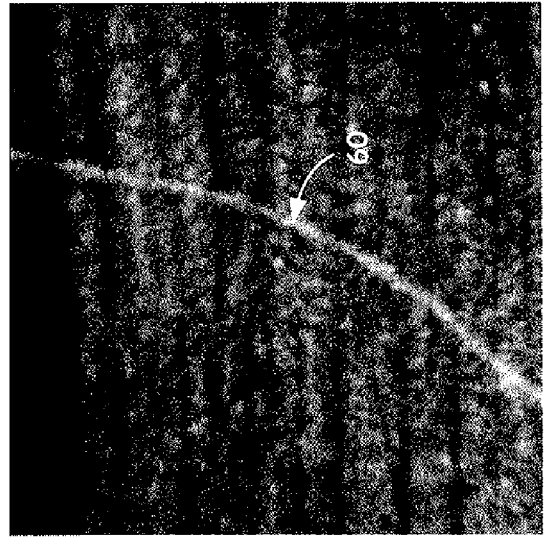
Fig. 4(b)
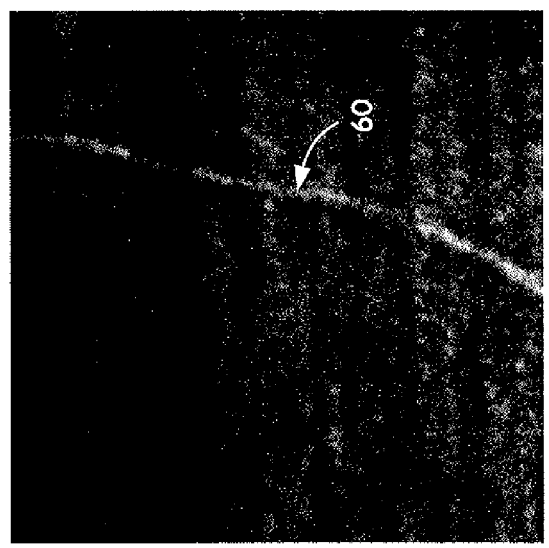
Fig. 4(a)
Fig. 4

HIGH-RESOLUTION ADAPTIVE OPTICS SCANNING LASER OPHTHALMOSCOPE WITH MULTIPLE DEFORMABLE MIRRORS

RELATED APPLICATION

This application claims priority from U.S. Provisional Patent Application No. 60/852,857, also entitled "High Resolution Adaptive Optics Scanning Laser Opthalmoscope with Multiple Deformable Mirrors," filed on Oct. 18, 2006, the disclosure of which is incorporated by reference in its entirety.

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to medical devices, more particularly the present invention is directed to adaptive optic scanning laser opthalmoscope (AOSLO) apparatus and methods configured with a plurality of deformable mirrors so as to compensate for optical aberrations in the eye under examination.

2. Description of Related Art

Adaptive optics has been utilized in a range of fields, such as, but not limited to remote sensing, atmospheric communications, correction of high power laser systems, and retinal imaging. With respect to retinal imaging, current adaptive optic systems and methods incorporate optical beams that are directed into the eye to form a spot on the retina and the reflected light is used to measure the aberrations that degrade the optical quality of the eye. Such measured aberrations can then be used to either improve the resolution of the deconvoluted retinal images or guide laser ablation apparatus for refractive surgery or provide the necessary information for eye spectacle prescription.

As another conventional arrangement, such measurements are used in real time to correct the measured aberrations with a single adaptive mirror. However, current technology cannot deliver the phase compensation needed using a single deformable mirror (DM) in a compact AOSLO system. Specifically, such single DM systems cannot collectively correct low-order aberrations with relatively large amplitudes while also correcting high-order aberrations with lower amplitudes so as to provide the necessary real-time ocular aberration corrections to achieve diffraction-limited in-vivo retinal images.

Background information for an adaptive optic scanning laser system using a single deformable mirror is described and claimed in U.S. Pat. No. 7,118,216 B2 entitled "Method And Apparatus For Using Adaptive Optics In A Scanning Laser Opthalmoscope," issued Oct. 10, 2006, to Roorda, including the following, "A scanning laser opthalmoscope incorporates adaptive optics to compensate for wavefront aberrations in the eye. Light from a light source is scanned onto the retina. Light reflected from the retina is detected for imaging and is also used for wavefront sensing. The sensed wavefront aberrations are used to control an adaptive optic device, such as a deformable mirror, disposed in the path of the light from the source in order to compensate for the aberrations."

Accordingly, a need exists for improved AOSLO methods and systems having at least two deformable optical components to provide real-time ocular aberration corrections in order to achieve diffraction-limited in-vivo retinal images. The present invention is directed to such a need.

SUMMARY OF THE INVENTION

Accordingly, the present invention is directed to a retinal imaging method that includes: optically scanning in two dimensions the entrance pupil of an eye so that an area of one or more retinal structures of the eye can be individually imaged; detecting one or more high-order and large-stoke low-order optical aberrations from a predetermined retinal structure resulting from scanning of the eye; providing at least two adaptive optical components, wherein at least one of the plurality of adaptive optical components is configured to correct for the one or more high order optical aberrations and at least one of the adaptive optical components is configured to correct for the one or more large-stroke low order optical aberrations; and feedback controlling in real time the at least two adaptive optical elements to compensate for the one or more high and the large-stroke low order optical aberrations in the light scanned on the area of the retinal structures so that the directed light is focused on desired predetermined retinal structures of the eye and so that the one or more high and the large-stroke low order optical aberrations are corrected for imaging the one or more retinal structures of the eye.

Another aspect of the present invention is directed to an optical apparatus, i.e., Adaptive Optics Scanning Laser Opthalmoscope (AOSLO) for real-time non-invasive examination of one or more layers of the human retina. The beneficial aspect of the present system is directed to the use of dual deformable mirrors to effectively compensate high-order and low-order aberrations in the human eye while maintaining the quality of the retinal imagery, wherein a predetermined deformable mirror improves the capability for axial sectioning with the confocal imaging system by providing an easier way to move the focus axially through different layers of the retina.

Accordingly, the present invention provides optical arrangements and methods to provide: high resolution diffraction-limited in-vivo retinal imaging and effective real-time ocular aberration corrections in a compact, transportable assembly for the clinical environment.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 2(a) shows a retinal image acquired without aberration corrections.

FIG. 2(b) shows a retinal image acquired having a predetermined deformable mirror (DM) turned on in a closed-loop operation.

FIG. 2(c) shows a retinal image acquired having a predetermined deformable mirror (DM) (e.g., the Micro-Electro-Mechanical Systems (MEMS) adaptive optic (AO)) turned on in a closed-loop operation.

FIG. 4(a) shows an image of blood vessel layer using the apparatus and methods of the present invention.

FIG. 4(b) shows an image of a nerve fiber layer using the apparatus and methods of the present invention.

DETAILED DESCRIPTION OF THE INVENTION

Figure 1:
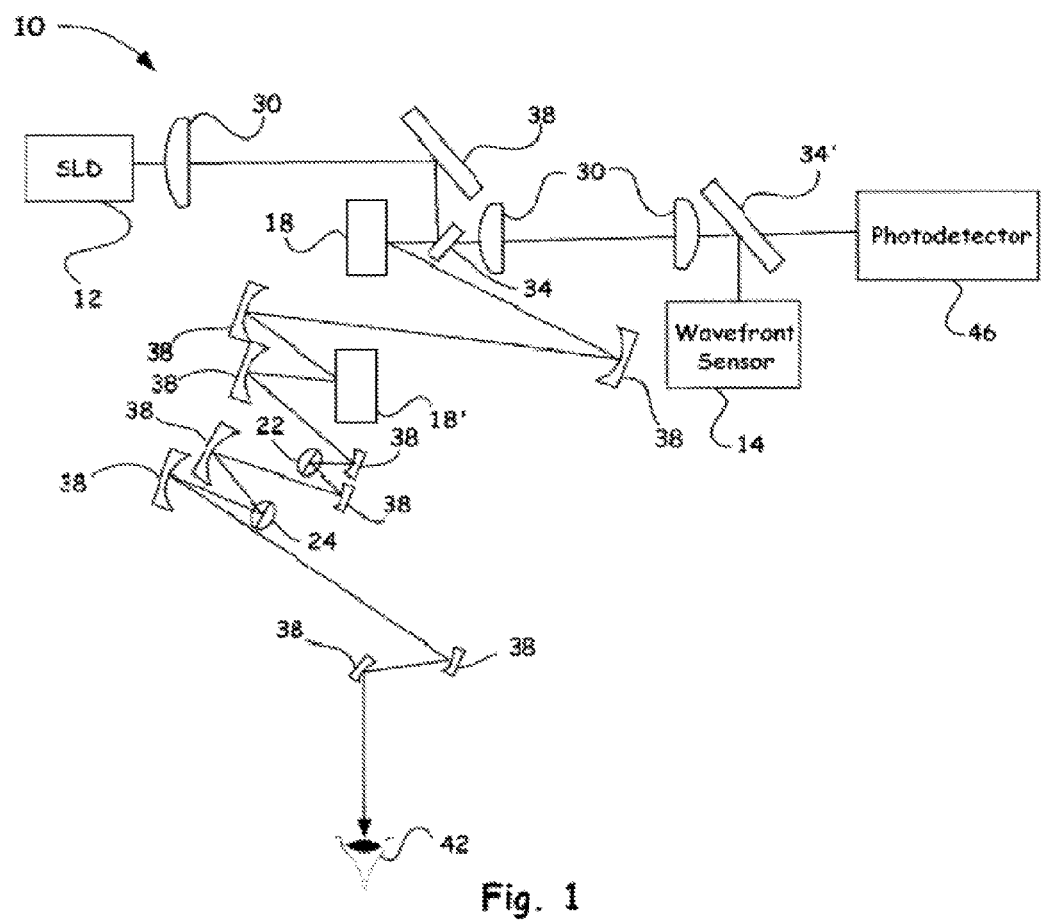
FIG. 1 shows a simplified diagram of an Adaptive Optics Scanning Laser Opthalmoscope (AOSLO) system of the present invention.

Referring now to the drawings, specific embodiments of the invention are shown. The detailed description of the specific embodiments, together with the general description of the invention, serves to explain the principles of the invention.

Unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

Specific Description

Optical System

The key goals for the optical system design of the present invention are (1) high resolution imaging, (2) effective ocular aberration correction, and (3) compact, transportable assembly for the clinical environment.

Turning now to the drawings, FIG. 1 shows a top view of the plurality deformable Adaptive Optical Scanning Laser Opthalmoscope (AOSLO) system, more often a dual deformable mirror Adaptive Optical Scanning Laser Opthalmoscope (dual-DM AOSLO) system of the present invention, generally designated by the reference numeral 10. The optical system(s), as disclosed herein, often comprises of several functional groups, such as, but not limited to, one or more optical sources 12, such as, but not limited to, one or more a Superluminescent Laser Diodes (SLDs)), a wavefront sensing unit 14, a wavefront compensation section 18 and 18' (e.g., a plurality of Adaptive Optics), a scanning optical system (e.g., an X-scanner 22 and a Y-scanner 26), one or more transport optics, such as, but not limited to, lenses 30, beamsplitters 34 and 34', and reflective optics 38 (e.g., spherical mirrors, flat mirrors, parabolic mirrors, etc.) to beam shape and direct optical radiation along predetermined optical paths, and a detection unit 42, all configured to produce a retinal image from a living eye 46.

Ocular aberration correction is achieved by placing the wavefront sensing unit 14, often a Shack-Hartmann wavefront sensor and at least two deformable mirrors 18 and 18' (DMs) at planes conjugate to the pupil of the eye 46. Each component is placed at the image plane of an afocal relay telescope 32. To reduce back reflections, mirrors 38, more often spherical mirrors, instead of lenses, are used in the afocal telescope designs. This has the additional benefit of eliminating chromatic aberrations in the system, which is important because the system is designed to operate at different wavelengths greater than 600 nm, often at 843 nm and/or 682 nm, which is often predicated on the imaging goals. One of the issues in using reflective spherical mirrors is that the off-axis configuration introduces astigmatism. This problem is solved by optimizing the system design and adding a cylindrical compensation lens (not shown) in the AOSLO.

Horizontal (e.g., X-scanner 22) and vertical scanners (e.g., Y-scanner 24) are also placed at planes conjugate to the pupil of the eye 42 to minimize the motion of the beam at the pupil as it scans across the retina. The reflected light from the retina travels back along the same path as the incoming illumination to the two scanners and the two DMs, and is finally separated by a pellicle beamsplitter 34' to both the wavefront sensor 14 and photodetector 46. An optical aperture (not shown) is placed at the focal point of the final relay telescope to reduce the stray light in the AOSLO. A confocal pinhole (not shown) is placed at the focal point of the collection lens. All the optical components can be assembled on a 2'×3' optical breadboard, mounted on a cart with wheels so that the opthalmoscope can be easily moved to different offices in a medical environment, such as, an opthalmology clinic.

Light Delivery

Because the AOSLO system 10 of the present invention, as shown in FIG. 1, is highly confocal, speckle can generate unwanted noise into the images. To reduce the speckle effects, optical sources 12, as shown in FIG. 1, are preferably low coherent light sources than lasers with very narrow linewidths. Two desired light sources, superluminescent diodes (SLD) from Superlum SLD-371-HP2-DBUT-SM-PD ($\lambda_0$=843.3 nm, $\Delta\lambda$=48.3 nm, P=18 mW) and SLD-261-HP1-DIL-SM-PD ($\lambda_0$=682 nm, $\Delta\lambda$=9.6 nm, P=5 mW) are often used in the AOSLO as disclosed herein. Both light sources are fiber coupled. A compact package, comprising of a fiber coupled single mode fiber connector, an x-y-z stage for adjusting the collimation lens, an achromatic lens, and a system aperture, delivers collimated light of the desired wavelength into the AOSLO. The use of different wavelengths is accomplished by switching using methods known by those of ordinary skill in the art, the incoming optical fibers to the light delivery package.

Wavefront Sensing

Wavefront sensing and detection paths in the AOSLO are designed to share the same light path as far as possible to minimize the non-common path errors. The wavefront error is preferably measured with a Shack-Hartmann wavefront sensor 14 that is configured with a 20×20 lenslet array (Adaptive Optics Associates, 0500-30-S-A, 500 um pitch, 30 mm focal length) and a Charge Coupled Device (CCD) camera (not shown in FIG. 1) (Dalsa 1M60 CCD CameraLink) at its focal plane. The wavefront sensor measures displacements of the spots produced by the lenslet array from its reference position. An adaptive optic (AO) coupled computer (not shown) reads the displacements and determines the wavefront errors in the optical paths.

Wavefront Compensation

At least two deformable mirrors (e.g., 18 and 18', as shown in FIG. 1) are employed to provide the wavefront compensation in the AOSLO 10, of the present invention. Both deformable mirrors 18 and 18', as shown in the example arrangement of FIG. 1, are placed at the planes conjugate to the entrance pupil of the eye 42 and to the wavefront sensor 14. The AO control computer receives the signals from the Shack-Hartmann wavefront sensor and sends signals to both deformable mirrors 18 and 18'.

A bimorph deformable mirror (Aoptix Technologies, Inc.), e.g., mirror 18, is used to correct large-stroke aberrations. Such a mirror design, as disclosed herein, often comprises layers of ceramic lead magnesium niobate that are actuated by the electrodes bonded on the material. A beneficial deformable mirror of the present invention includes 35 actuators which can be divided into two groups: curvature actuators and slope actuators. For the 35-element mirror, actuators 1 to 19 are curvature actuators, which produce curvature proportional to the applied voltage in the wavefront. Actuators 20 to 35 are slope actuators, which produce a radial slope proportional to the applied voltages in the wavefront. Actuator 20 is a guard ring which ensures a clean separation between curvature and slope actuators. The bimorph deformable mirror can achieve a displacement of up to about 16 µm over a 10 mm aperture, which can compensate up to 32 µm in wavefront phase. Because the stroke of the bimorph scales with the inverse square of the spatial frequency of the Zernike mode, and the highest spatial frequency mode is 5 cycles/diameter, the bimorph mirror is best used to compensate the large-stoke, low-order ocular aberrations.

The residual, high-order, small-stroke aberrations are beneficially corrected by a Micro-ElectroMechanical Systems (MEMS) mirror, preferably a MEMS Boston Micromachine, Inc. mirror. Such a mirror design comprises of a continuous membrane, supported by an underlying actuator array of 12×12 elements with a 300 µm pitch. Unlike the bimorph deformable mirror, each actuator is individually addressable and cross-talk between actuators is relatively small. The bimorph deformable mirror can achieve a displacement of up to about 1.5 µm over a 3.3 mm×3.3 mm area, which can compensate up to 3 µm in wavefront phase. The bimorph and MEMS deformable mirrors are conjugated to each other. Such conjugate planes are optically relayed in order to have the 10 mm pupil of the bimorph mirror matched to the 3.3 mm pupil of the MEMS mirror, and later to the pupil of the eye.

Deformable mirrors are designed to be carefully calibrated as optical "flats" before they are placed in the AOSLO system so that no additional aberration is introduced by the DMs. In the bimorph DM case, when no bias voltages are applied to the electrodes, the bimorph mirror has a natural curvature of 0.3 D due to the mechanical stress in the different layers of the mirror materials. The MEMS has an RMS error of 90 nm created by the non-uniformity in the manufacturing process. In the calibration set-up, a perfect collimated light source illuminates a configured DM and the wavefront error is measured by the Shack-Hartmann wavefront sensor. The DM under calibration is placed at the conjugate plane of the wavefront sensor lenslet array. The measured wavefront is used to calculate the voltages to be applied to the actuators of the DM to produce the desired shape. The iteration continues until the wavefront aberration is minimized and the AO operation stabilized. The AO computer saves the stabilized voltages and the shape of the DM is referenced as "Flat", which is the best experimental optical flat that can be achieved. The residual RMS error is 30 nm for the AOSLO system with the system "flats". About 10% of the total correction range of the deformable mirrors is used for the system "flats".

Turning now to the drawings, FIG. 1 shows a top view of the plurality deformable Adaptive Optical Scanning Laser Opthalmoscope (AOSLO) system, more often a dual deformable mirror Adaptive Optical Scanning Laser Opthalrnoscope (dual-DM AOSLO) system of the present invention, generally designated by the reference numeral 10. The optical system(s), as disclosed herein, often comprises of several functional groups, such as, but not limited to, one or more optical sources 12, such as, but not limited to, one or more a Superluminescent Laser Diodes (SLDs)), a wavefront sensing unit 14, a wavefront compensation section 18 and 18' (e.g., a plurality of Adaptive Optics), a scanning optical system (e.g., an X-scanner 22 and a Y-scanner 24), one or more transport optics, such as, but not limited to, lenses 30, beamsplitters 34 and 34', and reflective optics 38 (e.g., spherical mirrors, flat mirrors, parabolic mirrors, etc.) to beam shape and direct optical radiation along predetermined optical paths, and a detection unit 42, all configured to produce a retinal image from a living eye 46.

Scanning Optics

In the method of operation, the focused beam is scanned on the retina in a raster pattern with a horizontal X-scanner 22, preferably an Electro-Optics Products Corp., SC-30 resonate scanner, 14 kHz, 6°, and a vertical Y-scanner 24, preferably a Cambridge Technology, 6220M40 galvanometric scanner, ±20°. The two scanners are separated by a relay telescope as configured in the optical system of FIG. 1 so as to make them optically conjugate to each other and to the entrance pupil of the eye. This minimizes the movement of the scanning beam at the pupil, which is important for proper functioning of the AOSLO system. The optical design is optimized for a field of view of 2.9°×2.9° (optical scan angle) for a 6 mm circular eye pupil. The scanned image corresponds to a 0.9 mm×0.9 mm area on retina. The field of view is adjusted easily by changing the control voltages of the scanners.

If an object plane is at an angle to the principle axis of an optical system, its related image plane is formed at an angle to the principle axis. Thus, the optical conjugate plane of a scanner at the entrance pupil of the eye is not a fixed plane, but a rotating plane as a variable of the optical scanning angle. The Shack-Hartmann wavefront sensor measures the average aberrations over the integration time of the CCD camera. The combination of resonate scanner and galvanometric scanner provides raster images at 30 frame per second with 525 lines per frame.

Although the optical relay design attempts to minimize this effect, both horizontal and vertical scanners still produce some changes in beam properties at the entrance pupil of the eye. However, pupil shift and distortion can be minimized using designed tilt angles and spherical mirrors with longer focal lengths in the optical design optimization process.

It is to be noted that the beam locations and sizes are changing as a function of scan angle when using the dual DM AOSLO as disclosed herein. However, the wavefront measurement and compensation is not significantly affected as long as the change in beam footprints due to scanning is less than half of the subaperture. The maximum change allowed in the current AOSLO is 300 µm at the pupil plane of the eye to avoid wavefront registration errors and AO system performance degradation.

Image Detection

After the wavefront compensation with deformable mirrors, the light coming from the retina is focused through a confocal pinhole and detected with a detector, such as, for example, a GaAs photomultiplier tube (PMT) (H7422-50, Hamamatsu). An achromatic lens with a 150 mm focal length is can be configured to collect the light for the beam size of 10 mm in diameter. Axial resolution of the detected images is increased with the decreased pinhole size, while the light throughput is decreased with the decreased pinhole sizes. A beneficial pinhole size of 100 µm is often configured in the present AOSLO invention, which results in a 1.5× diffraction-limited spot size at the confocal plane. The 100-µm pinhole provides a good compromise between the axial resolution and light throughput for the dual DM AOSLO system. However, lateral resolution is set primarily by the point spread function (PSF) of the system, not by the size of the pinhole.

The photons are detected by the photodetector (e.g., the PMT) and the signal is fed to the frame grabber board. The frame grabber presents the raw image of 500×500 pixels at 27 frames per second. The extra lines from the raster scan images of 525 lines per frame are used for blanking and synchronization in the frame grabber.

Turning back to FIG. 1, in utilizing the system 10, a subject is asked to view a fixation target (not shown in FIG. 1) to minimize head and eye motion and to allow precise imaging of different retinal locations. An image from the wavefront sensor 14 is used to monitor the x-y position of the eye's 42 pupil. A bite-bar assembly (not shown) is mounted on an x-y-z translation stage on the optical table to permit precise positioning of the subject's eye 42. To ensure the maximum pupil size and minimize fluctuations in accommodation, the subject's eye is dilated and cyclopleged with 2.5% Phenylephrine and 1% Tropicamide for a 6 mm pupil.

The retinal image session starts with the wavefront measurement, then closing the control loop with the bimorph mirror for the initial phase compensation. After the wavefront is stabilized, closing the control loop with the MEMS deformable mirror to compensate the residual aberrations. Once the wavefront aberrations are minimized, the digital video recording is started.

Results

Imaging with and without AO Correction

The dual-deformable-mirrors AOSLO of the present invention was experimentally utilized in a clinical setting, at the University of California, Davis Medical Center, to image both healthy and diseased eyes.

FIGS. 2(a), 2(b) and 2(c) show the retinal images acquired from a healthy subject at the same retinal position with and without aberration corrections using the dual deformable mirrors (note blood vessel 60 in each image). In particular, FIG. 2(a) shows an image without AO correction while FIG. 2(b) shows an image having the first DM (i.e., the Bimorph AO 18, as shown in FIG. 1) turned on in a closed-loop operation, and FIG. 2(c) shows an image having the second DM (i.e., the MEMS AO 18', as shown in FIG. 1) turned on in a closed-loop operation. The resultant images were taken with an 843 nm SLD. The imaging position was at the retinal location of 3° Nasal and 3° Superior and the field of view is 1.1°×1.1°.

Figure 3:
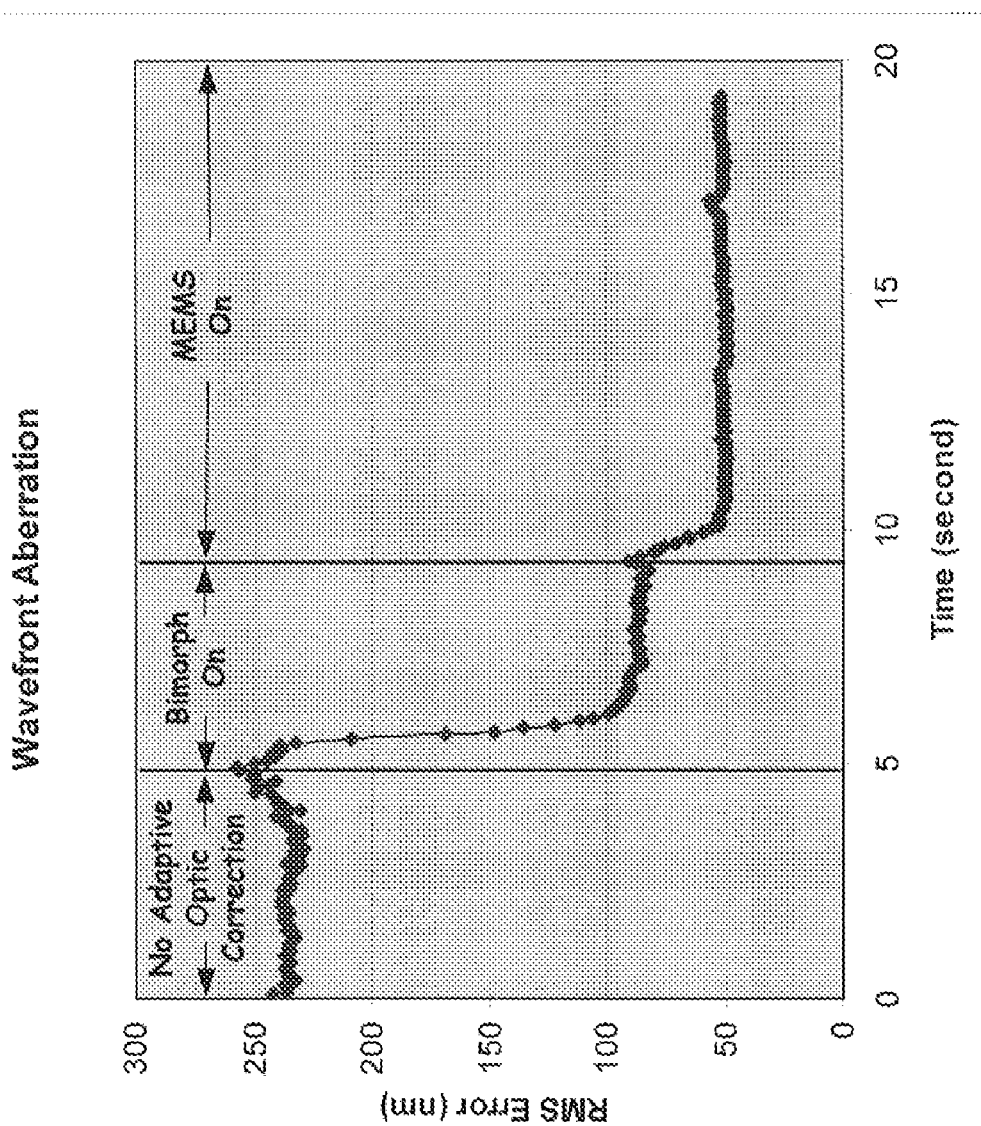
FIG. 3 shows the related RMS wavefront errors with and without the AO corrections.

FIG. 3 shows the related RMS wavefront errors with and without the AO corrections. The RMS wavefront error without AO was 248 nm over 6 mm pupil, and it was reduced to 90 nm when the first deformable mirror was turned on. The MEMS DM further reduced the RMS wavefront error to 48 nm. Strehl ratio is defined by the ratio of the intensity at the peak of the aberrated diffraction pattern to the intensity at the peak of an aberration-free image. Based on the measured aberrations, the Strehl ratio at the imaging wavelength (843 nm) is increased from 2% without AO correction to 55% with the first AO correction and 89% with the second AO correction. The AO corrected images showed higher resolution and increased brightness as the RMS wavefront error decreased with the AO correction.

Focus on Targeted Layers of Retina

FIGS. 4(a) and 4(b) show images acquired at the same retinal position when focusing on different layers of the retina as the images shown in FIG. 2. Such focusing is accomplished by adding a calculated difference vector to the measured reference vector for the wavefront sensor. Consequently, when the AO computer as utilized herein calculated the voltages to be applied to the actuators of the bimorph DM (e.g. adaptive optic (AO) 18, as shown in FIG. 1), optical curvature was applied to the mirror so that targeted layers of retina were in focus. When the closed-loop operation with the bimorph mirror (adaptive optic (AO) 18) was stable, the MEMS DM (adaptive optic (AO) 18'), was used to further reduce the high-order aberrations. After applying this additional correction, the images became brighter.

In particular, FIG. 4(a) shows the images of blood vessel layer and FIG. 4(b) show the images of the nerve fiber layer while FIG. 2 show the images of the photoreceptor layer. Comparing these three images, the blood vessel 60 appears darker in the images of FIG. 2. This is because the blood vessel layer was not in focus and the scattered light from its surface was blocked by the confocal pinhole when the photoreceptor layer was imaged. The total thickness of the retina is about 300 µm.

In acquiring the images of FIG. 4(a) and FIG. 4(b), image acquisition started from the photoreceptor layer, and then the image was focused on the blood vessel layer by biasing the bimorph mirror, e.g., AO 18. The blood cells could be clearly seen flowing through the vessel. Then, larger curvature was applied to the bimorph mirror 18 and the optical nerve fiber layer of FIG. 4(b) came into focus. The blood vessel layer and optical nerve fiber layer were close to the same optical plane, thus they are resolved at the same time.

When the closed-loop operation with the bimorph mirror was stable, the MEMS DM was used to further reduce the high-order aberrations. After applying this additional correction, the images of optical nerve fiber became brighter.

The dual DM AOSLO system provides high-resolution imaging capability of any desired layers of retina. This multilayer imaging capability can effectively save clinicians time and effort for imaging and diagnosis of retinal disease in the clinical environment.

It has been demonstrated that multiple micro-deformable mirrors in an AOSLO system can effectively compensate both large, low-order and small, high-order aberrations in the human eye, and produce in vivo retinal images with nearly diffraction-limited resolution. Focusing through different layers of the retina is also made possible by the use of large-stroke micro-deformable mirrors. Furthermore, the small size of the DM's enables a compact optical design, making the AOSLO system a viable, transportable, non-invasive, high-resolution imaging tool for clinical diagnostics.

Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The invention claimed is:

1. A retinal imaging method, comprising:
optically scanning in two dimensions the entrance pupil of an eye so that an area of one or more retinal structures of said eye can be individually imaged;
detecting one or more high-order and large-stoke low-order optical aberrations from a predetermined said retinal structure resulting from scanning of said eye;
providing at least two adaptive optical components, wherein at least one of said plurality of adaptive optical components is configured to correct for said one or more high order said optical aberrations and at least one of said adaptive optical components is configured to correct for said one or more large-stroke low order said optical aberrations; and feedback controlling in real time said at least two adaptive optical elements to compensate for said one or more high and said large-stroke low order optical aberrations in the light scanned on the area of said retinal structures so that the directed light is focused on desired said predetermined retinal structures of said eye and so that said one or more high and said large-stroke low order optical aberrations are corrected for imaging said one or more retinal structures of said eye.

2. The method of claim 1, wherein said adaptive optical components are controlled to provide axial sectioning of said one or more retinal structures of said eye.

3. The method of claim 2, wherein said adaptive optical component comprises a bimorph mirror.

4. The method of claim 3, wherein said bimorph mirror corrects for one or more said large-stroke low-order optical aberrations.

5. The method of claim 1, wherein said adaptive optical components comprises a Micro-electromechanical system (MEMS).

6. The method of claim 5, wherein said Micro-electromechanical systems (MEMS) mirror corrects for one or more said high-order optical aberrations.

7. The method of claim 1, wherein said detecting step comprises a Hartmann-Shack detector.

8. The method of claim 7, wherein said detecting step comprises a Charge Coupled Device.

9. A system for imaging a retinal structure of an eye, comprising:

an electromagnetic source configured to direct an output radiation into a predetermined optical path;

a two-dimensional scanning section for performing a transverse two-dimensional scan of a focused spot of said radiation at a pupil plane of an eye;

a detection section configured to measure one or more high-order and one or more large-stroke low-order optical aberrations resultant from scattered radiation of scanned one or more retinal structures of said eye;

at least two adaptive optical components interposed in said predetermined optical path, said at least two adaptive optical components being directed to correct for measured said one or more high order and said large-stroke low order optical aberrations resulting from scanned said one or more retinal structures of said eye so that a corrected focused spot can be directed onto desired said one or more retinal structures and so that said one or more high order and low order optical aberrations produced in said scattered radiation can be corrected for imaging purposes; and a detector configured to image said one or more retinal structures of said scanned eye.

10. The system of claim 9, wherein the system is optimized for a field of view of 2.9°×2.9° for a 6 mm circular eye pupil.

11. The system of claim 9, wherein a resultant scanned image corresponds to a 0.9 mm×0.9 mm area on said one or more retinal structures of said eye.

12. The system of claim 9, wherein said at least two adaptive optical components comprises a deformable mirror.

13. The system of claim 12, wherein said deformable mirror comprises a bimorph mirror.

14. The system of claim 13, wherein said bimorph provides for axial sectioning.

15. The system of claim 13, wherein said bimorph mirror corrects for one or more said large-stroke low-order optical aberrations.

16. The system of claim 15, wherein said bimorph mirror comprises a displacement of up to about 16 μm over about a 10 mm aperture so that up to about 32 μm in wavefront phase can be compensated.

17. The system of claim 12, wherein said deformable mirror comprises a Micro-electromechanical system (MEMS).

18. The system of claim 17, wherein said Micro-electromechanical systems (MEMS) mirror corrects for said one or more said high-order optical aberrations.

19. The system of claim 17, wherein said Micro-electromechanical systems (MEMS) mirror comprises a plurality of actuators selected from: curvature actuators and slope actuators.

20. The system of claim 19, wherein said actuators comprises up to about 35-elements, wherein actuators 1 to 19 are curvature actuators to produce curvature proportional to the applied voltage in the wavefront, and wherein actuators 20 to 35 are slope actuators to produce a radial slope proportional to the applied voltages in the wavefront.

21. The system of claim 9, wherein said detection section comprises a Hartmann-Shack detector.

22. The system of claim 9, wherein said detection section comprises a Charge Couple Device (CCD).

23. The system of claim 9, wherein said detection section comprises a photodetector and a beam splitter configured along a principal optical axis to direct optical radiation reflected from the retina between the Hartmann-Shack detector and the photodetector.

24. The system of claim 12, wherein said output radiation comprises low coherent light sources having desired narrow line-widths so that speckle effects are minimized.

25. The system of claim 12, wherein said output radiation comprises wavelengths greater than about 600 nm.

* * * * *